(12) United States Patent
Dunmire

(10) Patent No.: US 10,154,857 B1
(45) Date of Patent: Dec. 18, 2018

(54) MICRODERMABRASION SYSTEM

(71) Applicant: Rebecca C. Dunmire, Palm Harbor, FL (US)

(72) Inventor: Rebecca C. Dunmire, Palm Harbor, FL (US)

( * ) Notice: Subject to any disclaimer, the term of this patent is extended or adjusted under 35 U.S.C. 154(b) by 88 days.

(21) Appl. No.: 14/550,469

(22) Filed: Nov. 21, 2014

(51) Int. Cl.
*A61B 17/54* (2006.01)
*A61B 17/32* (2006.01)
*A61B 17/00* (2006.01)

(52) U.S. Cl.
CPC .............. *A61B 17/54* (2013.01); *A61B 17/32* (2013.01); *A61B 2017/0046* (2013.01); *A61B 2017/00424* (2013.01); *A61B 2017/00477* (2013.01); *A61B 2017/00761* (2013.01); *A61B 2017/320004* (2013.01)

(58) Field of Classification Search
CPC ....... A61B 2017/320004; A61B 2017/320008; A61B 2017/320012; A61B 2017/00424; A61B 2017/0046; A61B 2017/00477; A61B 17/54; A61B 17/32; A61B 2017/00761; A61B 17/320004
USPC ......................................................... 606/131
See application file for complete search history.

(56) References Cited

U.S. PATENT DOCUMENTS

| | | | | |
|---|---|---|---|---|
| 5,088,509 A * | 2/1992 | Savage, III | ............ | A45D 29/04 132/73.5 |
| 6,178,970 B1 * | 1/2001 | Purifoy | .................. | A61B 17/54 132/73.5 |
| 6,363,944 B1 * | 4/2002 | Stangenberg | .......... | A61B 17/54 132/75.3 |
| 8,226,662 B2 * | 7/2012 | Song | ...................... | A61B 17/54 132/76.4 |
| 2005/0103357 A1 * | 5/2005 | Jo | ........................... | A61B 17/54 132/76.4 |
| 2005/0216034 A1 * | 9/2005 | Lind | ...................... | A61B 17/54 606/131 |
| 2006/0015124 A1 * | 1/2006 | Floerke | ................... | A61B 17/54 606/131 |
| 2006/0058714 A1 * | 3/2006 | Rhoades | .............. | A45D 24/007 601/73 |
| 2007/0208354 A1 * | 9/2007 | Barraclough | .......... | A45D 26/00 606/133 |
| 2007/0244491 A1 * | 10/2007 | Russell | ................... | A61B 17/54 606/131 |
| 2007/0293795 A1 * | 12/2007 | Carroll | ................... | A61B 17/54 606/131 |
| 2008/0091216 A1 * | 4/2008 | Grace | ................... | A61B 17/54 606/131 |
| 2008/0293795 A1 * | 11/2008 | Donawho | .......... | A61K 31/4184 514/394 |
| 2009/0124985 A1 * | 5/2009 | Hasenoehrl | ............ | A45D 34/04 604/289 |

(Continued)

*Primary Examiner* — Jing Ou

(57) ABSTRACT

Left and right bodies coupled together create a chamber interiorly and form a handle exteriorly. Each of the bodies has a closed proximal end and an open distal end and retention fingers adjacent to the open distal end. A replaceable head has a proximal end and a distal end. The proximal end of the replaceable head has toothed projections removably received by the retention fingers. The distal end of the replaceable head has an oval shaped section. A medical grade adhesive tape has an interior surface adhesively attached to the oval shaped section of the replaceable head and has an exterior surface with an abrasive layer.

1 Claim, 8 Drawing Sheets

(56) References Cited

U.S. PATENT DOCUMENTS

| | | | |
|---|---|---|---|
| 2009/0157094 A1* | 6/2009 | Yeshurun | A61B 17/54 606/131 |
| 2009/0192442 A1* | 7/2009 | Ignon | A61M 35/003 604/22 |
| 2010/0323810 A1* | 12/2010 | Kaneko | A63B 53/10 473/320 |
| 2012/0016379 A1* | 1/2012 | Kay | A61B 17/54 606/131 |
| 2015/0051620 A1* | 2/2015 | Presser | A61B 17/54 606/131 |

* cited by examiner

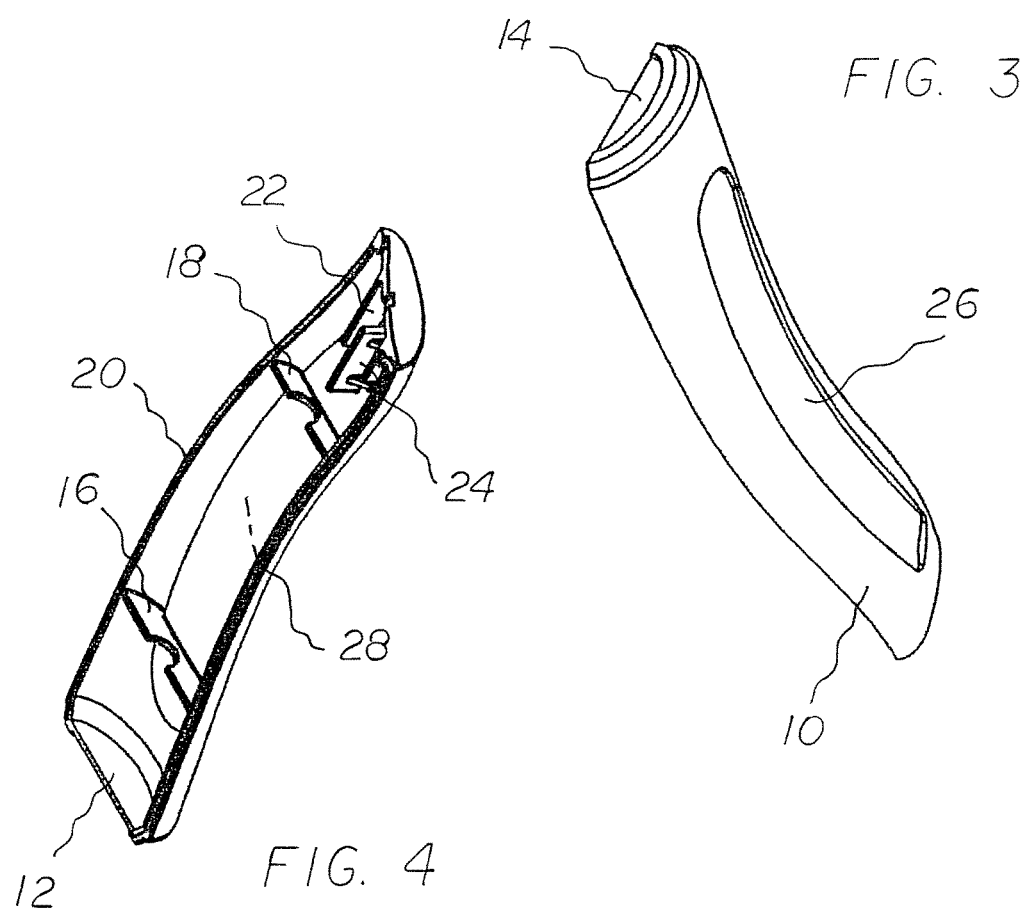

MICRODERMABRASION SYSTEM

BACKGROUND OF THE INVENTION

Field of the Invention

The present invention relates to a microdermabrasion system and more particularly pertains to abrading dead skin and for changing an abrading component in a safe, sanitary, convenient, and economical manner.

Description of the Prior Art

The use of microdermabrasion systems of known designs and configurations is known in the prior art. More specifically, microdermabrasion systems of known designs and configurations previously devised and utilized for the purpose of abrading dead skin are known to consist basically of familiar, expected, and obvious structural configurations, notwithstanding the myriad of designs encompassed by the crowded prior art which has been developed for the fulfillment of countless objectives and requirements.

More specifically, disadvantages of current microderm systems may include: complicated vacuum suctions that often become clogged, the need for power outlets and/or continued recharging, the need for sterilization/risk of cross-contamination if not properly sterilized, size of small microderm tip that can take considerable time to complete the procedure, and high cost associated with other microderm devices.

While these devices fulfill their respective, particular objectives and requirements, they do not describe microdermabrasion system that allows abrading dead skin and for changing an abrading component in a safe, sanitary, convenient, and economical manner.

In this respect, the microdermabrasion system according to the present invention substantially departs from the conventional concepts and designs of the prior art, and in doing so provides an apparatus primarily developed for the purpose of abrading dead skin and for changing an abrading component in a safe, sanitary, convenient, and economical manner.

Therefore, it can be appreciated that there exists a continuing need for a new and improved microdermabrasion system which can be used for abrading dead skin and for changing an abrading component in a safe, sanitary, convenient, and economical manner. In this regard, the present invention substantially fulfills this need.

SUMMARY OF THE INVENTION

In view of the foregoing disadvantages inherent in the known types of microdermabrasion systems of known designs and configurations now present in the prior art, the present invention provides an improved microdermabrasion system. As such, the general purpose of the present invention, which will be described subsequently in greater detail, is to provide a new and improved microdermabrasion system and method which has all the advantages of the prior art and none of the disadvantages.

To attain this, from a broad standpoint, the present invention essentially comprises left and right bodies coupled together to create a chamber interiorly and form a handle exteriorly. Each of the bodies has a closed proximal end and an open distal end and retention fingers adjacent to the open distal end. A replaceable head has a proximal end and a distal end. The proximal end of the replaceable head has toothed projections removably received by the retention fingers. The distal end of the replaceable head has an oval shaped section. A medical grade adhesive tape has an interior surface adhesively attached to the oval shaped section of the replaceable head and has an exterior surface with an abrasive layer.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved microdermabrasion system which has all of the advantages of the prior art microdermabrasion systems of known designs and configurations and none of the disadvantages.

It is another object of the present invention to provide a new and improved microdermabrasion system which may be easily and efficiently manufactured and marketed.

It is a further object of the present invention to provide a new and improved microdermabrasion system which is of durable and reliable constructions.

An even further object of the present invention is to provide a new and improved microdermabrasion system which is susceptible of a low cost of manufacture with regard to both materials and labor, and which accordingly is then susceptible of low prices of sale to the consuming public, thereby making such microdermabrasion system economically available to the buying public.

Lastly, another object of the present invention is to provide a microdermabrasion system for abrading dead skin and for changing an abrading component in a safe, sanitary, convenient, and economical manner.

These together with other objects of the invention, along with the various features of novelty which characterize the invention, are pointed out with particularity in the claims annexed to and forming a part of this disclosure.

For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a perspective illustration of the left body of FIG. 2.

FIG. 4 is a perspective illustration of the right body of FIG. 2.

The same reference numerals refer to the same parts throughout the various Figures.

DESCRIPTION OF THE PREFERRED EMBODIMENT

Figure 1:
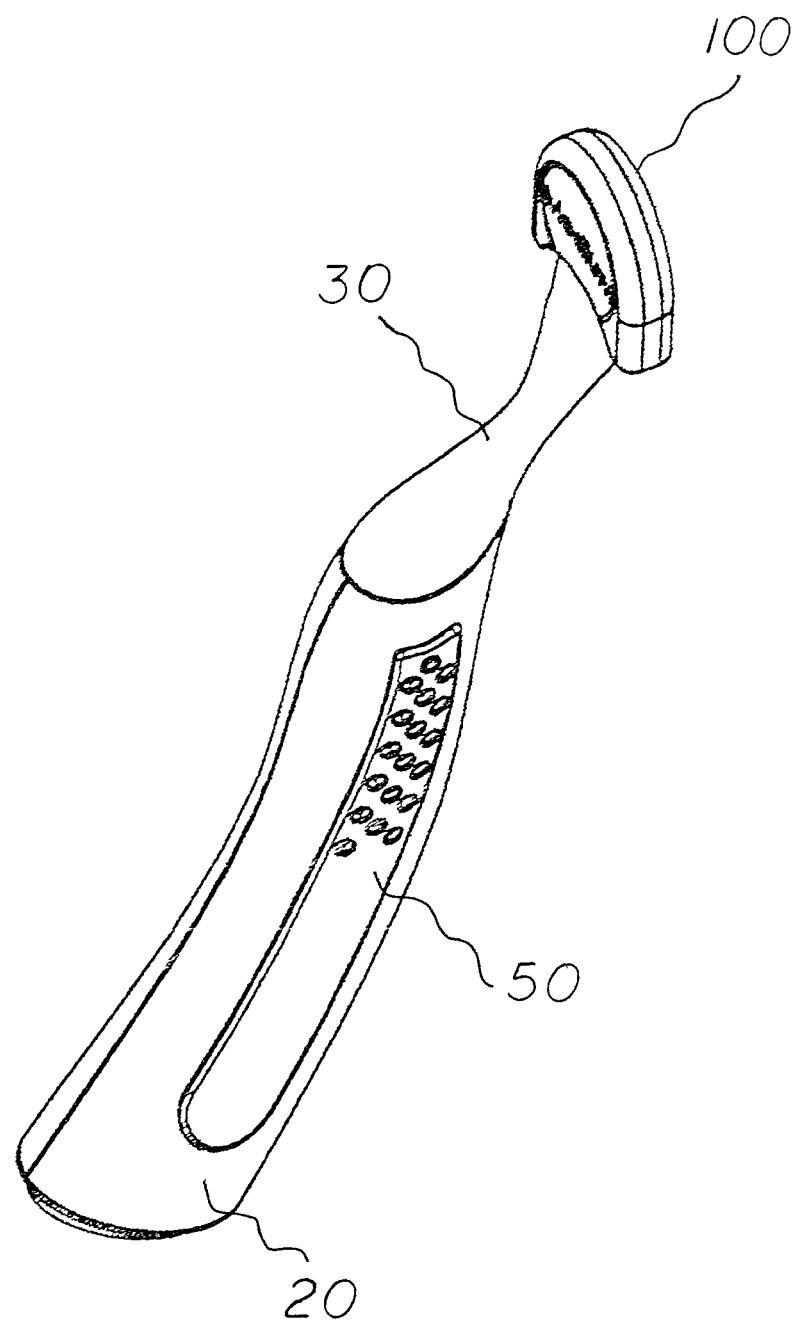
FIG. 1 is a perspective illustration of a microdermabrasion system constructed in accordance with the principles of the present invention.
Figure 2:
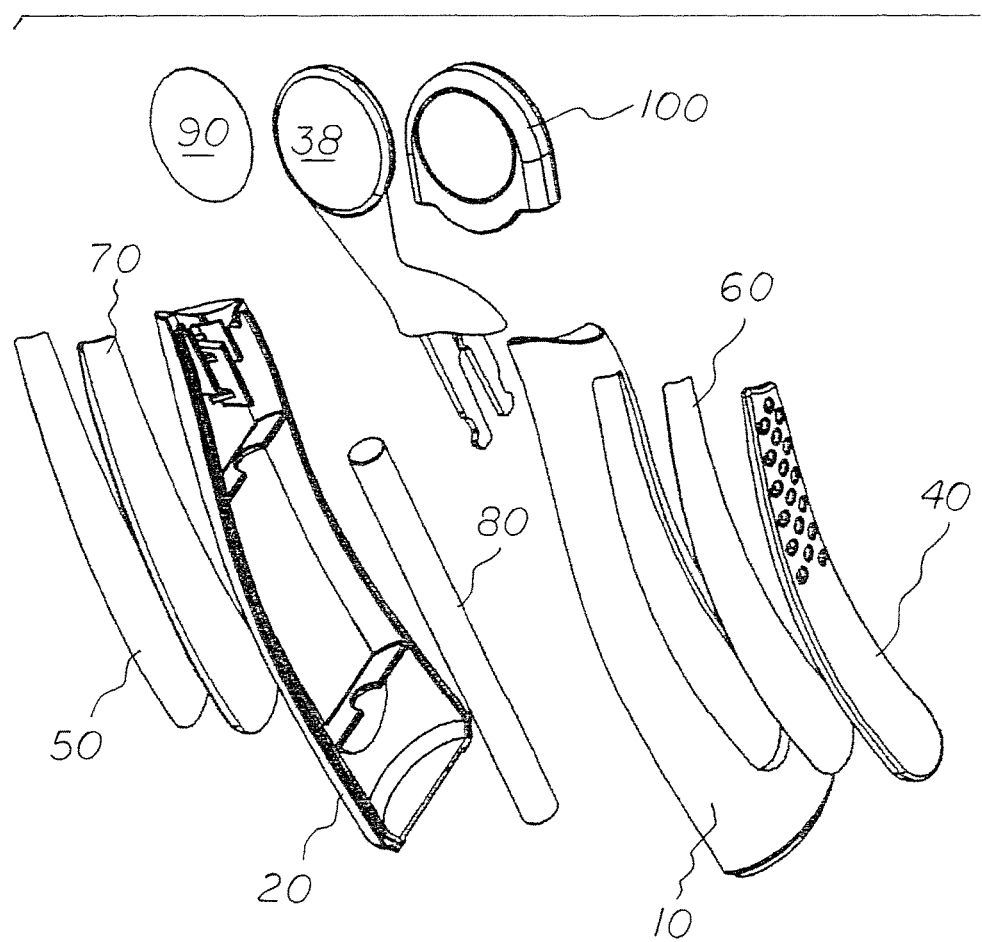
FIG. 2 is an exploded perspective illustration of the system shown in FIG. 1.
Figure 5:
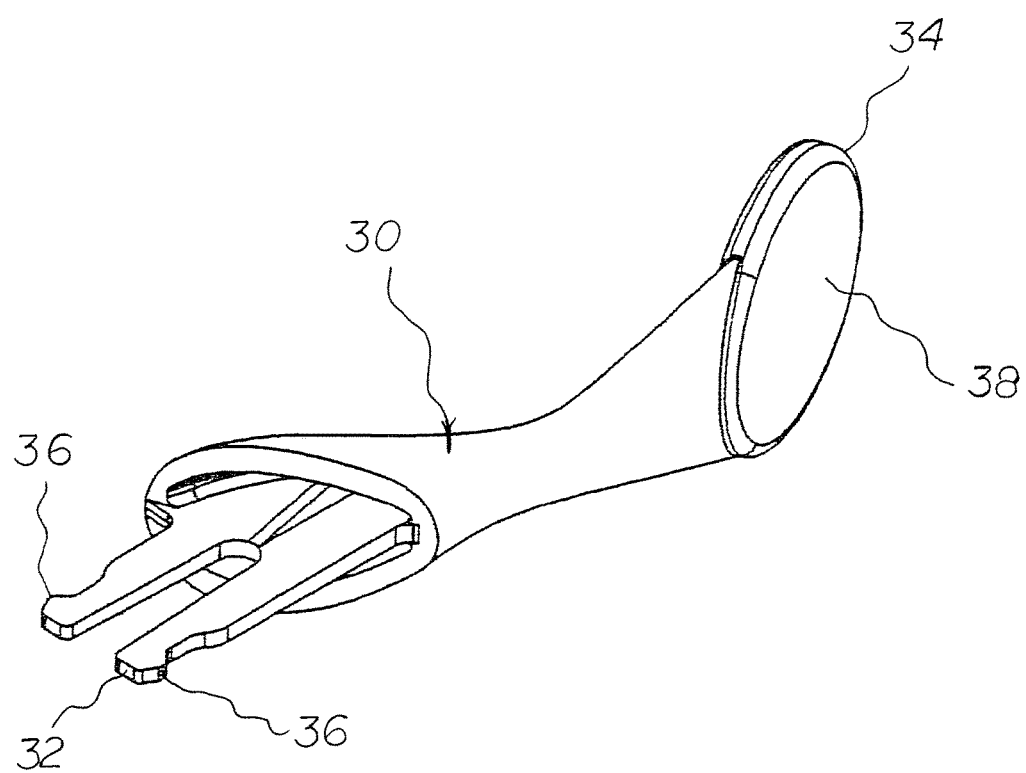
FIG. 5 is a perspective illustration of the replaceable head of FIG. 2.
Figures 6, 7:
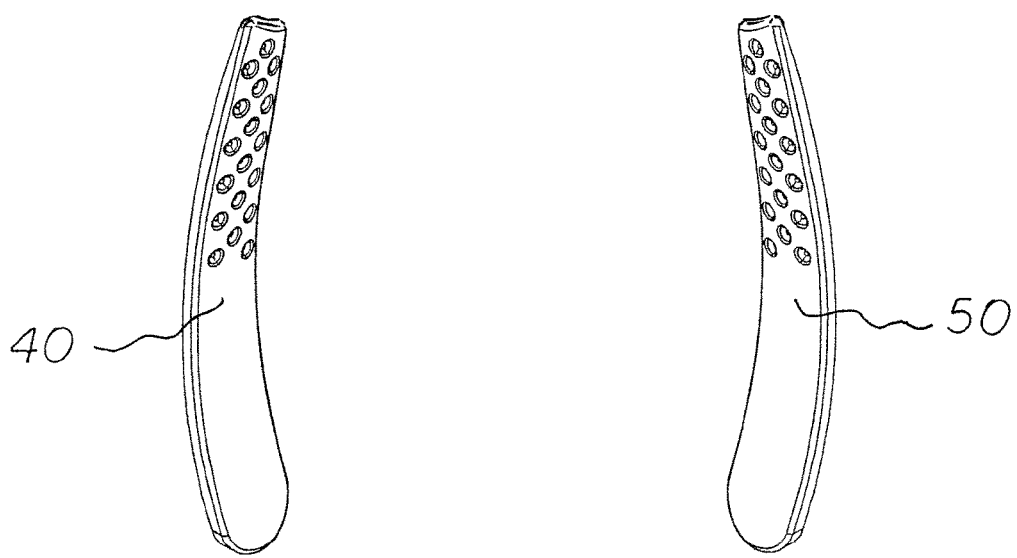
FIG. 6 is a perspective illustration of the left rubber grip of FIG. 2.
FIG. 7 is a perspective illustration of the right rubber grip of FIG. 2.
Figures 8, 9:
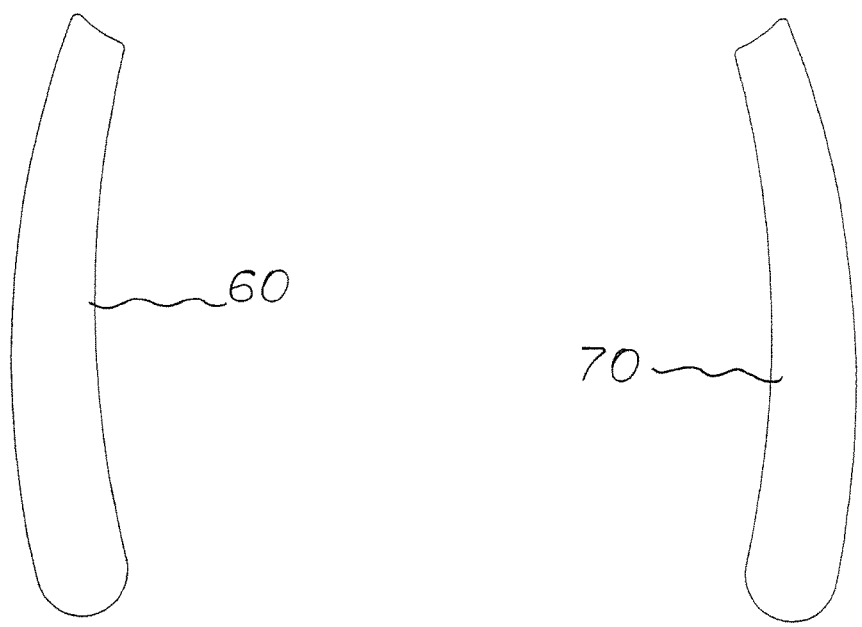
FIG. 8 is a perspective illustration of the left double sided tape of FIG. 2.
FIG. 9 is a perspective illustration of the right double sided tape of FIG. 2.
Figure 10:
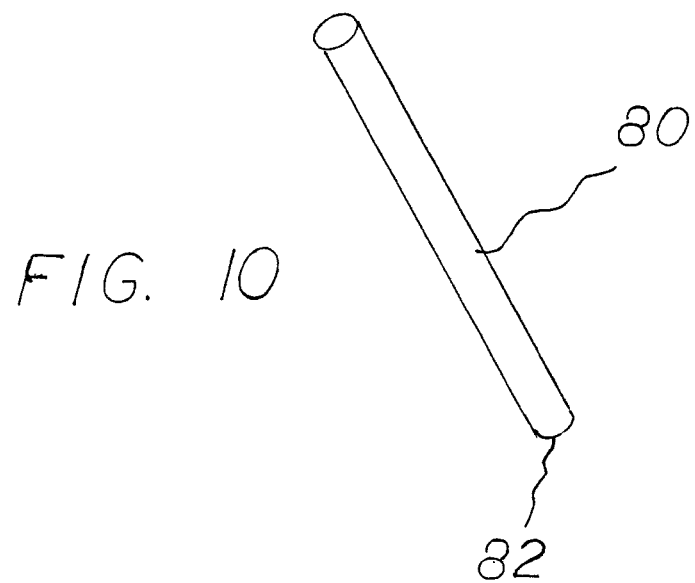
FIG. 10 is a perspective illustration of the steel plated cylindrical weight of FIG. 2.
Figure 11:
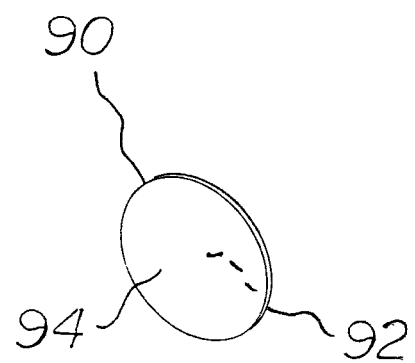
FIG. 11 is a perspective illustration of the adhesive tape of FIG. 2.
Figure 12:
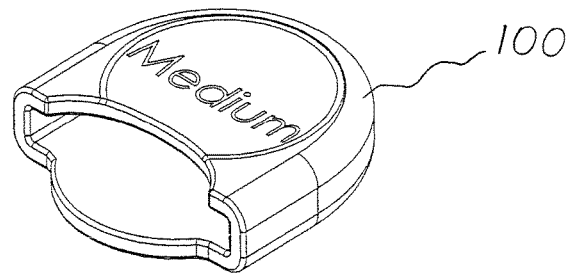
FIG. 12 is a perspective illustration of the protective boot of FIG. 2.
Figure 13:
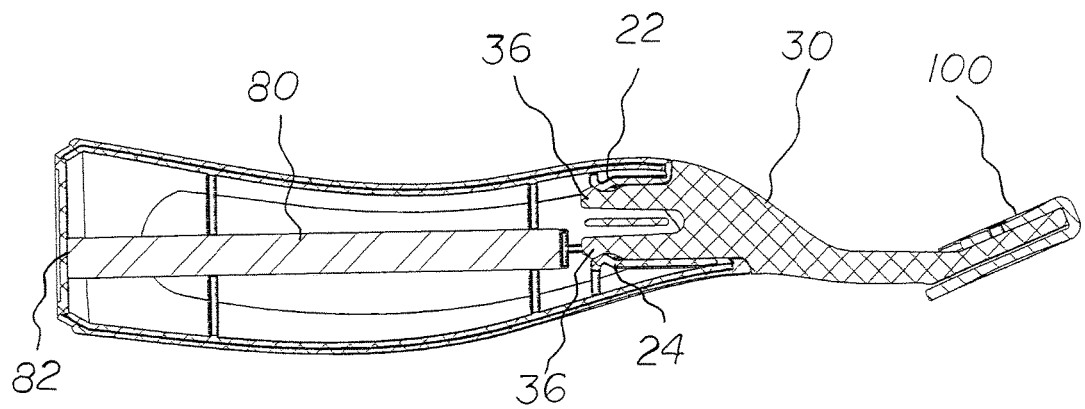
FIG. 13 is a cross sectional view taken axially through the system illustrated in FIG. 1.

With reference now to the drawings, and in particular to FIG. 1 thereof, the preferred embodiment of the new and improved microdermabrasion system embodying the principles and concepts of the present invention and generally designated by the reference numeral 10 will be described.

The present invention, the microdermabrasion system 10 is comprised of a plurality of components. Such components in their broadest context include a left body and a right body, a replacement head, and a medical grade adhesive tape. Such components are individually configured and correlated with respect to each other so as to attain the desired objective.

The microdermabrasion system of the present invention is for abrading dead skin and for changing an abrading component. The abrading and the changing are done in a safe, sanitary, convenient, and economical manner.

From a specific standpoint, a left body 10 and a similarly configured right body 20 are provided. The left body and the right body each have a closed proximal end 12 and an open distal end 14. The left body and the right body each have a first support plate 16 with a semi-circular cutout. The left body and the right body each have a second support plate 18 with a semi-circular cutout. The left body and the right body each have a first retention finger 22 and a radially spaced second retention finger 24 adjacent to the open distal end. The left body and the right body are coupled together to create a chamber interiorly and to form a handle exteriorly. The handle has a left side recess 26 and a right side recess 28.

Next provided is a replaceable head 30 having a proximal end 32 and a distal end 34. The proximal end has toothed projections 36 positionable in the open distal end of the left body and the right body and removably received by the first retention fingers and the second retention fingers. The distal end of the replaceable head extends distally from the handle with an oval shaped section 38.

Next a left rubber grip 40 is provided. The left rubber grip is secured in the left side recess of the handle. Also provided is a right grip 50 secured in the right side recess of the handle.

A left double sided adhesive tape 60 is provided between the left rubber grip and the left side recess of the handle for attachment purposes. A right double sided adhesive tape 70 is provided between the right rubber grip and the right side recess of the handle for attachment purposes.

Next provided is a weight 80. The weight has a cylindrical configuration with a proximal end 82 in contact with the closed proximal end of the left body and the closed proximal end of the right body. The weight has a distal end adjacent to the open distal end of the left body and the open distal end of the right body. The weight has a cylindrical surface received by and in contact with the semi-circular cutouts of the first support plate and the semi-circular cutouts of the second support plate. The weight is fabricated of plated steel.

Next provided is a medical grade adhesive tape 90 having an interior surface 92 and an exterior surface 94. The interior surface is adhesively attached to the oval shaped section of the replaceable head. The exterior surface has an abrasive layer of aluminum oxide and zeolite and a medical grade adhesive.

A protective boot 100 is next provided. The protective boot is adapted to removably receive the replaceable head and the medical grade adhesive tape. The left body and the right body and the replaceable head and the protective boot are fabricated of plastic.

From the above it may be realized that the present invention, a crystal smooth system, offers advantages absent from the prior art. Such advantages include: (1) a removable head recommended to be replaced after each use, thus more sanitary than other microderm systems, and more convenient as it does not require sterilization; (2) the abrasive layer includes aluminum oxide and zeolite, a mineral used to absorb impurities from the skin, something that other systems do not offer; (3) Increased convenience due to no need for batteries, or recharging; and (4) due to the nature of the system, it is easier to control the pressure on the skin, thus not causing too much abrasion of the skin.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A microdermabrasion system for abrading dead skin and for changing an abrading component, the abrading and the changing being done in a safe, sanitary, convenient, and economical manner, the system consisting of:

a left body (10) and a similarly configured right body (20), the left body and the right body each having a closed proximal end (12) and an open distal end (14), the left body and the right body each having a first support plate (16) with a semi-circular cutout, the left body and the right body each having a second support plate (18) with a semi-circular cutout, the left body and the right body each having a first retention finger (22) and a radially spaced second retention finger (24) adjacent to the open distal end, the left body and the right body being coupled together to create a chamber interiorly and to form a handle exteriorly, the handle having a left side recess (26) and a right side recess (28);

a replaceable head (30) having a proximal end (32) and a distal end (34), the proximal end having toothed projections (36) positionable in the open distal end of the left body and the right body and removably received by the first retention fingers and the second retention fingers, the distal end of the replaceable head extending distally from the handle with an oval shaped section (38);

a left rubber grip (40) secured in the left side recess of the handle, a right grip (50) secured in the right side recess of the handle;

a left double sided adhesive tape (60) between the left rubber grip and the left side recess of the handle for attachment purposes, a right double sided adhesive tape (70) between the right rubber grip and the right side recess of the handle for attachment purposes;

a weight (80) having a cylindrical configuration with a proximal end (82) in contact with the closed proximal end of the left body and the closed proximal end of the right body, the weight having a distal end adjacent to the open distal end of the left body and the open distal end of the right body, the weight having a cylindrical surface received by and in contact with the semi-circular cutouts of the first support plates and the semi-circular cutouts of the second support plates, the weight being fabricated of plated steel;

a medical grade adhesive tape (90) having an interior surface (92) and an exterior surface (94), the interior surface adhesively attached to the oval shaped section of the replaceable head, the exterior surface having an abrasive layer of aluminum oxide and zeolite and medical grade adhesive; and a protective boot (100) adapted to removably receive the replaceable head and the medical grade adhesive tape, the left body and the right body and the replaceable head and the protective boot being fabricated of plastic.

\* \* \* \* \*